United States Patent
Bazhenov et al.

(10) Patent No.: US 11,480,933 B2
(45) Date of Patent: Oct. 25, 2022

(54) NEURAL NETWORKS FOR OCCUPIABLE SPACE AUTOMATION

(71) Applicants: Maksim Bazhenov, Rancho Santa Fe, CA (US); Maxim Komarov, San Diego, CA (US); Nikolai Romanov, Oak Park, CA (US)

(72) Inventors: Maksim Bazhenov, Rancho Santa Fe, CA (US); Maxim Komarov, San Diego, CA (US); Nikolai Romanov, Oak Park, CA (US)

(*) Notice: Subject to any disclaimer, the term of this patent is extended or adjusted under 35 U.S.C. 154(b) by 517 days.

(21) Appl. No.: 16/608,847

(22) PCT Filed: Apr. 30, 2018

(86) PCT No.: PCT/US2018/030102
§ 371 (c)(1),
(2) Date: Oct. 27, 2019

(87) PCT Pub. No.: WO2018/201120
PCT Pub. Date: Nov. 1, 2018

(65) Prior Publication Data
US 2020/0209810 A1  Jul. 2, 2020

Related U.S. Application Data

(60) Provisional application No. 62/491,734, filed on Apr. 28, 2017.

(51) Int. Cl.
*G05B 13/02* (2006.01)
*G06N 3/04* (2006.01)
(Continued)

(52) U.S. Cl.
CPC ............. *G05B 13/027* (2013.01); *A61N 1/36* (2013.01); *G05B 13/026* (2013.01);
(Continued)

(58) Field of Classification Search
CPC ................ G05B 13/027; G05B 13/026; G05B 2219/2642; G05B 15/02; A61N 1/36; A61N 1/05; G06N 3/0445; G06N 3/08
(Continued)

(56) References Cited

U.S. PATENT DOCUMENTS

2014/0379625 A1  12/2014 Modha et al.
2016/0075034 A1  3/2016 Laurent et al.
(Continued)

OTHER PUBLICATIONS

International Search Report and Written Opinion for International Patent Application No. PCT/US2018/30102, dated Aug. 8, 2018, 10 pages.
(Continued)

*Primary Examiner* — Charlotte M Baker
(74) *Attorney, Agent, or Firm* — Withrow & Terranova, P.L.L.C.; Vincent K. Gustafson

(57) ABSTRACT

Provided herein is a system for occupiable space automation using neural networks that delivers scalable and more intelligent occupiable space automation that can continuously learn from user actions and experiences and adapt to specific needs of each individual occupiable space. The occupiable space automation control system is built based on brain inspired multi-layer neural network with plastic connectivity between neurons. The occupiable space automation control system is configured to (a) adaptively predict previously learned activity patterns and (b) alert about potentially harmful or undesired activity patterns of the plurality of periphery devices based on response events of the plurality of artificial neurons and coupling strengths of the plurality of synapses. The occupiable space automation control system is configured to automatically operate the at least one controller based on the predicted activity pattern and/or provide user alerts based on a detected harmful activity pattern.

20 Claims, 8 Drawing Sheets

(51) Int. Cl.
  *G06N 3/08* (2006.01)
  *A61N 1/36* (2006.01)
  *A61N 1/05* (2006.01)

(52) U.S. Cl.
  CPC ............. *G06N 3/0445* (2013.01); *G06N 3/08* (2013.01); *A61N 1/05* (2013.01)

(58) Field of Classification Search
  USPC ......................................................... 706/23
  See application file for complete search history.

(56) References Cited

U.S. PATENT DOCUMENTS

| | | |
|---|---|---|
| 2016/0156771 A1 | 6/2016 | Lee |
| 2018/0268292 A1* | 9/2018 | Choi .................... G06K 9/6264 |
| 2019/0384790 A1* | 12/2019 | Bequet .............. G06F 16/90344 |

OTHER PUBLICATIONS

International Preliminary Report on Patentability for International Patent Application No. PCT/US2018/30102, dated Apr. 28, 2017, 9 pages.

Bazhenov, M., et al., (2013) "A Computational Framework for Understanding Decision Making through Integration of Basic Learning Rules," The Journal of Neuroscience, Mar. 27, 2013, 33(13), pp. 5686-5697.

Komarov, M. et al., "Adaptive Functional Systems: Learning with Chaos," Chaos: An Interdisciplinary Journal of Nonlinear Science, American Institute of Physics, http://dx.doi.org/10.1063/1.3521250, 2010, pp. 20:045119-1-20:045119-9.

Skorheim, S. et al., "A Spiking Network Model of Decision Making Employing Rewarded STDP," PLOS ONE 9(3):e90821. https://doi.org/10.1371/journal.pone.0090821, Mar. 14, 2014, 17 pages.

* cited by examiner

NEURAL NETWORKS FOR OCCUPIABLE SPACE AUTOMATION

STATEMENT OF RELATED APPLICATION(S)

This application is a 35 U.S.C. § 371 national phase filing of International Application No. PCT/US2018/030102 filed on Apr. 30, 2018, and claims priority to U.S. Provisional Patent Application No. 62/491,734 filed on Apr. 28, 2017, wherein the entire contents of the foregoing applications are hereby incorporated by reference herein.

TECHNICAL FIELD

This disclosure relates to occupiable space automation. In particular, the present disclosure relates to neural networks for occupiable space automation (e.g., home automation and/or vehicle automation).

BACKGROUND

Home automation (HA), among other types of automation, is a growing industry. Many companies ranging from small start-ups to large corporations are developing various kinds of "smart" solutions for the home. Many of these efforts entail developing hardware platforms including a "typical" set of periphery devices (PDs) such as motion detectors, contact sensors, wall switches, outlet switches, thermostats, $CO_2$ sensors, etc. However, such efforts fail to deliver true smart automation, as they lack the ability to learn from user actions and control PDs based on past use patterns. Without such capability, even assuming rapid development and adoption of PDs in households, HA applications remain very limited. Some examples of limited HA applications include: 1) controlling home devices from smart phone solutions or other similar solutions, e.g., using smart phone to turn On/Off lights and other devices in the house; and 2) using programming tools to create simple "rules", e.g., linking specific event (e.g., wall switch or motion sensor in one area of the house) to control devices (e.g., lights in other area). Such applications have limited applicability for everyday use for a variety of reasons. In real life, using automation to simply control home devices may not be faster or more convenient than the "old/classic" approach. For example, turning lights on or off may entail a user retrieving and unlocking his/her smartphone, starting or navigating to a specific program, and activating a button associated with the program. The foregoing steps may be substantially more time-consuming for the user than the traditional approach of activating a conventional wall switch. Further, writing even very simple programs to control specific devices based on time or events would require more time, effort, and/or understanding than most consumers are willing to expend. For example, VCR programming schedules for recording specific television programs were not widely adopted for similar reasons. But even if it were feasible to apply a conventional programming solution to control a few devices, such programming would lack scalability necessary for deploying HA in real houses and commercial buildings with potentially hundreds of smart devices.

Current products do not provide seamless utilization of automated devices in a home environment or other occupiable spaces. In other words, current products can't "predict" user intentions and control devices without explicit use of controllers or programming tools.

Accordingly, there is a need for scalable and more intelligent occupiable space automation that can continuously learn from user actions and experiences adapting to the specific needs of each individual occupiable space (e.g., household).

No admission is made that any reference cited herein constitutes prior art. Applicant expressly reserves the right to challenge the accuracy and pertinence of any cited documents.

SUMMARY

Provided herein is a system for occupiable space automation using neural networks that can learn from user actions and experiences, and adapt to specific needs of each individual occupiable space, thereby delivering scalable and more intelligent automation. The occupiable space automation control system (which may also be referred to as an occupiable space automation control device or "brain device" (BD)) can achieve such functionality with little or no special setup or programming. In general terms, similar to the functioning of human and animal brains, a BD incorporates learning based on different plasticity mechanisms that make small changes of connectivity between neurons involved in the action that led to the desired outcome or are frequently repeated during a training phase. Thus, over time, the brain network forms a selected set of links between neurons that represent commonly occurring sequences of events or desired outcomes from sequences of events. Furthermore, a BD disclosed herein has advantages over machine learning algorithms (e.g., deep learning) by (a) being inherently parallel and therefore well-suited for implementation in specialized computational hardware (GPUs, FPGAs, etc.); (b) being able to be trained by a limited set of data; (c) being able to learn new data without destroying previously established data.

A BD may be built based on a brain inspired multi-layer neural network (also known as a "neuronal network") with plastic connectivity between units (neurons). In certain embodiments, a BD can be integrated with a variety of existing occupiable space automation hardware controllers (e.g., Homeseer, Verra, ISY, Smarthome). Different approaches to deploying this solution may include a local solution and a cloud solution. In certain embodiments, a local solution may be based on a local computer (general purpose PC, low cost dedicated computer (such as, e.g., Raspberry Pi, or embedded computer, etc.)) running software that analyzes user-specific patterns of behavior (e.g., as part of a learning phase) and provides feedback to an occupiable space automation controller after a sufficient period of learning (e.g., as part of a controlling phase). In certain embodiments, a cloud solution (e.g., employing a subscription-based service) may be provided where data from individual installations may be uploaded to a server where they are analyzed offline and subsequently downloaded to controllers of customers. In both cases, the occupiable space automation system provides seamless integration by learning silently in the background and then providing feedback and assistance.

In certain embodiments, a BD can serve at least two main functions including "Prediction" of user pattern (e.g., turning a light On at a specific time and in a specific location based on events) and "Alerts" of potentially dangerous deviations from a typical pattern.

With respect to "Predictions", in rich occupiable space automation environments and/or time, specific patterns of activity will be repeating. For example, in one exemplary pattern, approaching a home is followed by opening the garage, turning On a light switch in a hallway (at dusk), turning a TV On to specific channel, etc. Each such pattern would be reflected in a sequence of events such as: proximity sensor activation, garage contact sensor On, light On, TV On, etc. Observation of such patterns repeating a sufficient number of times will lead to its learning by the BD. After that initial phase, the BD can start predicting a sequence based on the initial part of the sequence (e.g., proximity sensor being activated within specific time window), and will complete the sequence (e.g., turn light On). The BD can also predict and execute expected actions based on events, time of day, weather conditions, etc. A BD is able to solve many difficulties, such as, for example, that a user may want light in the bedroom to be turned On only within a specific time window, or under other specific conditions. In certain embodiments, a user can further adjust and tune a configuration of a previously trained system by providing positive reinforcement (in case of a desired system response) and/or negative reinforcement (in case of an undesired system response). In certain embodiments, such reinforcement may include voice control through a voice recognition system.

With respect to "Alerts," significant deviations from one or more specific patterns of behavior can indicate a life-threatening situation or security breach. For example, having the front door or garage door opened on a rainy day or late at night, with such action never happening before within a normal pattern of behavior of specific user, may indicate health problem of a user currently at home. In another example, detection of activity within a house without being preceded by a normal sequence of events, such as opening of a garage door or a front door, may indicate a burglary event. The same BD capable of predicting next events in the sequence can detect those abnormal patterns and trigger corresponding activity, such as, for example, transmitting a text message to all users on a list or initiating emergency responder (e.g., "911") telephone calls.

In certain embodiments, a BD may label all events that never happened before as alarms. To avoid a huge flow of alerts, however, "importance" weights are assigned to different events. In one embodiment a user can manually assign weights or chose to completely ignore specific events after receiving a notification. Alternatively, or additionally, in certain embodiments, a user may train the system for events that are considered alarm-ish by the user. For example, a user can create an event with the garage door opened and Security system On (by actually physically opening the garage door and turning the alarm On) and then explicitly "click" the alert "button" to teach the system to interpret this as an alert situation. Such features may minimize or reduce false positive detections that are potentially costly and/or train the network for alarm events without actually require frequent occurrence of those events.

In one aspect, the disclosure relates to a system for occupiable space automation, the system comprising: a plurality of periphery devices operatively coupled with at least one controller configured to electronically control operation of at least one occupiable space device; and an occupiable space automation control system in electronic communication with the plurality of periphery devices, the occupiable space automation control system comprising a neural network of a plurality of artificial neurons interconnected by a plurality of synapses, the plurality of artificial neurons comprising a device layer associated with and configured to receive input from the plurality of periphery devices and comprising a context layer configured to receive at least one signal indicative of context conditions; wherein: each artificial neuron of the plurality of artificial neurons comprises a neuron state and a neural input threshold value, and each artificial neuron is configured to receive a first neural input, to alter the neuron state when the first neural input received at the artificial neuron crosses the neural input threshold value, and to initiate at least one response event dependent on the neuron state, the at least one response event providing at least one second neural input to other artificial neurons of the plurality of artificial neurons; each synapse of the plurality of synapses interconnects a different pair of artificial neurons, corresponding to the synapse, of the plurality of artificial neurons, and comprises a coupling strength that varies depending on response events of the corresponding pair of artificial neurons within a predetermined time window; the occupiable space automation control system is configured to adaptively predict a predicted activity pattern of the plurality of periphery devices based on response events of the plurality of artificial neurons and coupling strengths of the plurality of synapses; and the occupiable space automation control system is configured to automatically operate the at least one controller based on the predicted activity pattern.

In certain embodiments, the system is configured to automatically execute an operation upon detection of a deviation from the predicted activity pattern.

In certain embodiments, the plurality of periphery devices comprises at least one sensor. In certain embodiments, the plurality of periphery devices comprises at least one user-activated element. In certain embodiments, the plurality of periphery devices comprises at least one of a clock or a timer. In certain embodiments, the plurality of periphery devices comprises at least one of a camera or a microphone.

In certain embodiments, the context conditions comprise environmental or temporal conditions. In certain embodiments, the context conditions comprise environmental conditions, and the environmental conditions comprise geolocation conditions.

In certain embodiments, the plurality of artificial neurons comprises a complex connections layer associated with recurrent connections of the context layer and the device layer.

In certain embodiments, the coupling strength of at least one synapse of the plurality of synapses varies if response events of the corresponding pair of artificial neurons are generated within the predetermined time window. In certain embodiments, the coupling strength of at least one synapse of the plurality of synapses varies if response events of the corresponding pair of artificial neurons are not generated within the predetermined time window.

In certain embodiments, at least one synapse of the plurality of synapses comprises a coupling strength upper limit to require response events of the plurality of artificial neurons to exceed the neural input threshold value for at least one artificial neuron of the plurality of artificial neurons.

In certain embodiments, the system is configured to alter the neuron state when the first neural input and the at least one second neural input exceed the neural input threshold value. In certain embodiments, the system is configured to alter the neuron state when the first neural input and the at least one second neural input drop below the neural input threshold value.

In certain embodiments, the system is configured to receive a user override preventing the occupiable space automation control system from automatically operating the at least one controller based on the predicted activity pattern.

In certain embodiments, occupiable space of the occupiable space automation comprises a premises.

In certain embodiments, occupiable space of the occupiable space automation comprises a vehicle.

In another aspect, the disclosure relates to a method for occupiable space automation, the method comprising: electronically receiving, by at least one first artificial neuron of a device layer of a neural network of an occupiable space automation control system, input from at least one periphery device of a plurality of periphery devices; initiating, by the at least one first artificial neuron, a first response event generating a neural input; altering a neuron state of at least one second artificial neuron of a context layer of the neural network connected to the at least one first artificial neuron by a synapse if the neural input received by the at least one second artificial neuron crosses a neural input threshold value, wherein the context layer is configured to receive at least one signal indicative of context conditions; generating, by the at least one second artificial neuron, a second response event dependent on a neuron state of the at least one second artificial neuron; altering a neuron state of at least one third artificial neuron of the neural network that is connected by synapses to the at least one first and the at least one second artificial neurons, if a total neural input received by the at least one third artificial neuron from the at least one first and the at least one second artificial neurons crosses the neural input threshold value; generating, by the at least one third artificial neuron, a third response event dependent on a neuron state of the at least one third artificial neuron; varying a coupling strength of the synapse dependent on the first, second, and third response events occurring within a predetermined time window; adaptively predicting, by the occupiable space automation control system, a predicted activity pattern of the plurality of periphery devices based on the first, second, and third response events and the coupling strength of the synapse; and automatically operating, by the occupiable space automation control system, at least one controller of the plurality of periphery devices based on the predicted activity pattern to alter operation of at least one occupiable space device.

In certain embodiments, the foregoing first, second, and third neurons may be activated simultaneously, or with different delays (with such activation being either sequential or non-sequential in character). In certain embodiments, one or more of the at least one first artificial neuron, the at least one second artificial neuron, or the at least one third artificial neuron may include a plurality of neurons, wherein each neuron of a like type may be associated with a same or different device.

In certain embodiments, one or more artificial neurons may comprise a sensor. In certain embodiments, activation of at least one neuron may comprise activation of a plurality of neurons (e.g., a group of context layer neurons) configured to trigger a response in at least one device neuron. In certain embodiments, one or more specific environment neurons (e.g., time neurons) may be activated at specific times, depending on whether one or more neural input threshold values have been satisfied.

In certain embodiments, the at least one first artificial neuron comprises a device specific sensor neuron (e.g., a motion sensor), the at least one second artificial neuron comprises a specific environment neuron (e.g., a time neuron), and the at least one third artificial neuron comprises another device specific neuron (e.g., a controller, a light switch, or any home appliance). In certain embodiments, synapse strength varies from at least one sensor neuron to a controller, and synapse strength varies from at least one time neuron to a controller. In certain embodiments, a system or method exhibits a scaling rule for synaptic strength, such as the sum of the inputs to a third neuron is maintained to be constant, whereby response of a third neuron (e.g., a controller neuron) depends on multiple artificial neurons (e.g., a first sensor neuron and a second time neuron) exceeding one or more neural input threshold values. In such an embodiment, no single first (e.g., sensor) neuron or second (e.g., time neuron) neuron on its own may activate a third (e.g., controller) neuron; instead, only a combination of first and second neurons may produce a response.

In certain embodiments, the method further comprises automatically executing, by the occupiable space automation control system, an operation upon detection of a deviation from the predicted activity pattern.

In certain embodiments, the plurality of periphery devices comprises at least one sensor. In certain embodiments, the plurality of periphery devices comprises at least one user-activated element. In certain embodiments, the plurality of periphery devices comprises at least one of a clock or a timer. In certain embodiments, the plurality of periphery devices comprises at least one of a camera or a microphone.

In certain embodiments, the context conditions comprise environmental or temporal conditions. In certain embodiments, the environmental conditions comprise geolocation conditions.

In certain embodiments, varying the coupling strength of the synapse dependent on the first and third response events occurring within the predetermined time window comprises varying the coupling strength if the first and third response events are generated within the predetermined time window. In certain embodiments, varying the coupling strength of the synapse dependent on the second and third response events occurring within the predetermined time window comprises varying the coupling strength if the second and third response events are generated within the predetermined time window.

In certain embodiments, varying the coupling strength of the synapse dependent on the first and third response events occurring within the predetermined time window comprises varying the coupling strength if the first and third response events are not generated within the predetermined time window. In certain embodiments, varying the coupling strength of the synapse dependent on the second and third response events occurring within the predetermined time window comprises varying the coupling strength if the second and third response events are not generated within the predetermined time window.

In certain embodiments, the synapse comprises a coupling strength upper limit to require response events of a plurality of artificial neurons to exceed the neural input threshold value for at least one artificial neuron of the plurality of artificial neurons. In certain embodiments, the synapse comprises a coupling strength upper limit to require response events of a plurality of artificial neurons to exceed the neural input threshold value together by more than one artificial neuron of the plurality of artificial neurons.

In certain embodiments, altering the neuron state of the at least one second artificial neuron connected to the at least one first artificial neuron by the synapse if the neural input received by the at least one second artificial neuron crosses the neural input threshold value comprises altering the neuron state if the neural input received exceeds the neural input threshold value.

In certain embodiments, altering the neuron state of the at least one second artificial neuron connected to the at least one first artificial neuron by the synapse if the neural input received by the at least one second artificial neuron crosses the neural input threshold value comprises altering the neuron state if the neural input received drops below the neural input threshold value.

In certain embodiments, the automatically operating, by the occupiable space automation control system, of the at least one controller of the plurality of periphery devices based on the predicted activity pattern to alter operation of the at least one occupiable space device is responsive to input received from the at least one periphery device of the plurality of periphery devices.

In certain embodiments, occupiable space of the occupiable space automation comprises a premise.

In certain embodiments, occupiable space of the occupiable space automation comprises a vehicle.

In another aspect, the disclosure relates to a non-transitory computer readable medium comprising program instructions for occupiable space automation, wherein the program instructions are configured for: electronically receiving, at a first artificial neuron of a device layer of a neural network of an occupiable space automation control system, input from at least one periphery device of a plurality of periphery devices; initiating, by the first artificial neuron, a first response event generating a neural input; altering a neuron state of a second artificial neuron of a context layer of the neural network connected to the first artificial neuron by a synapse if the neural input received by the second artificial neuron crosses a neural input threshold value, wherein the context layer is configured to receive at least one signal indicative of context conditions; generating, by the second artificial neuron, a second response event dependent on the neuron state; varying a coupling strength of the synapse dependent on the first and second response events occurring within a predetermined time window; adaptively predicting, by the occupiable space automation control system, a predicted activity pattern of the plurality of periphery devices based on the first and second response events and the coupling strength of the synapse; and automatically operating, by the occupiable space automation control system, at least one controller of the plurality of periphery devices based on the predicted activity pattern to alter operation of at least one occupiable space device.

In certain embodiments, the program instructions further comprise automatically executing, by the occupiable space automation control system, an operation upon detection of a deviation from the predicted activity pattern.

In certain embodiments, the plurality of periphery devices comprises at least one sensor. In certain embodiments, the plurality of periphery devices comprises at least one user-activated element. In certain embodiments, the plurality of periphery devices comprises at least one of a clock or a timer. In certain embodiments, the plurality of periphery devices comprises at least one of a camera or a microphone.

In certain embodiments, the context conditions comprise environmental or temporal conditions. In certain embodiments, the environmental conditions comprise geolocation conditions.

In certain embodiments, varying the coupling strength of the synapse dependent on the first and second response events occurring within the predetermined time window comprises varying the coupling strength if the first and second response events are generated within the predetermined time window. In certain embodiments, varying the coupling strength of the synapse dependent on the first and second response events occurring within the predetermined time window comprises varying the coupling strength if the first and second response events are not generated within the predetermined time window.

In certain embodiments, the synapse comprises a coupling strength upper limit to require response events of a plurality of artificial neurons to exceed the neural input threshold value for at least one artificial neuron of the plurality of artificial neurons.

In certain embodiments, altering the neuron state of the second artificial neuron connected to the first artificial neuron by the synapse if the neural input received by the second artificial neuron crosses the neural input threshold value comprises altering the neuron state if the neural input received exceeds the neural input threshold value.

In certain embodiments, altering the neuron state of the second artificial neuron connected to the first artificial neuron by the synapse if the neural input received by the second artificial neuron crosses the neural input threshold value comprises altering the neuron state if the neural input received drops below the neural input threshold value.

In certain embodiments, the automatically operating, by the occupiable space automation control system, of the at least one controller of the plurality of periphery devices based on the predicted activity pattern to alter operation of the at least one occupiable space device is responsive to input received from the at least one periphery device of the plurality of periphery devices.

In certain embodiments, occupiable space of the occupiable space automation comprises a premise.

In certain embodiments, occupiable space of the occupiable space automation comprises a vehicle.

In still another aspect, the disclosure relates to a system for occupiable space automation, the system comprising: a plurality of periphery devices operatively coupled with at least one controller configured to electronically control operation of at least one occupiable space device; and an occupiable space automation control system in electronic communication with the plurality of periphery devices, the occupiable space automation control system comprising a neural network configured to receive input from the plurality of periphery devices and configured to receive at least one signal indicative of context conditions; wherein the occupiable space automation control system is configured to adaptively predict a predicted activity pattern of the plurality of periphery devices based on use of the plurality of periphery devices over time; and wherein the occupiable space automation control system is configured to automatically operate the at least one controller based on the predicted activity pattern.

In certain embodiments, the occupiable space automation control system is configured to automatically execute an operation upon detection of a deviation from the predicted activity pattern.

In certain embodiments, the plurality of periphery devices comprises at least one sensor.

In certain embodiments, the neural network adaptively predicts the predicted activity pattern at least partially based on context condition data.

In certain embodiments, an association between two periphery devices of the plurality of periphery devices varies if the two periphery devices are used within a predetermined time window. In certain embodiments, an association between two periphery devices of the plurality of periphery devices varies if the two periphery devices are not used within a predetermined time window.

In certain embodiments, operation of a target periphery device of the plurality of periphery devices requires simultaneous activation of at least two conditions of the context conditions.

In certain embodiments, the occupiable space automation control system is configured to automatically operate the at least one controller based on the predicted activity pattern and in response to an electronic input received from at least one periphery device of the plurality of periphery devices.

In certain embodiments, the occupiable space automation control system is configured to receive a user override preventing the occupiable space automation control system from automatically operating the at least one controller based on the predicted activity pattern.

In certain embodiments, the context conditions comprise environmental or temporal conditions. In certain embodiments, the environmental conditions comprise geolocation conditions.

In certain embodiments, occupiable space of the occupiable space automation comprises a premise.

In certain embodiments, occupiable space of the occupiable space automation comprises a vehicle.

In certain aspects, any of the foregoing aspects or other features disclosed here may be combined for additional advantage.

Those skilled in the art will appreciate the scope of the present disclosure and realize additional aspects thereof after reading the following detailed description of the preferred embodiments in association with the accompanying drawing figures.

DETAILED DESCRIPTION

Figure 1:
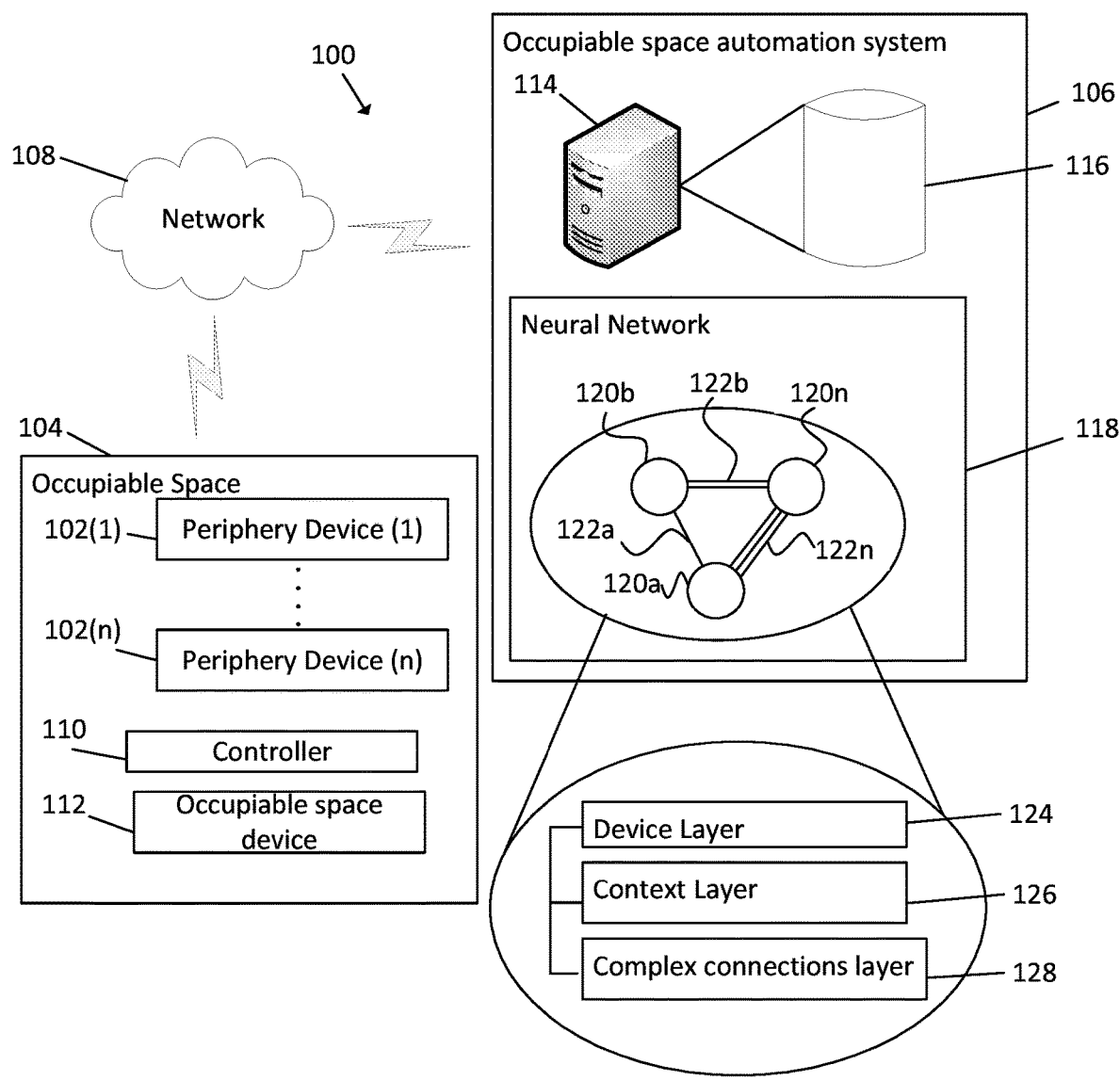
FIG. 1 is a schematic diagram of an occupiable space automation system according to one embodiment of the present disclosure.

Provided herein is a neural network based "brain device" (BD) that occupiable space automation can learn from user actions and experiences (i.e., past pattern of user behavior) adapting to specific needs of each individual occupiable space. The BD comprises an array of base units (wherein may also be referred to herein as "neurons") connected by the coupling elements (which may also be referred to as "synapses"). Each periphery device (PD) (e.g., a light switch, motion sensor, contact sensor, etc.), that is part of the installation will be represented by at least one, or possibly many, neurons. It is noted that the term "periphery devices," as used herein may include one or more sensors, controllers, and/or occupiable space devices. More complex devices, such as thermostats, sprinkler controllers, home entertainment systems, appliances, etc., may also be represented by multiple neurons. In addition, a BD can include any number of additional neurons not directly associated with any specific PDs. The coupling elements can change their properties (which may be referred to herein as "learning") based on the system experience.

An occupiable space may embody any of a variety of spaces (e.g., areas, locations, rooms, etc.) that may be occupied by one or more people. For example, in certain embodiments, the occupiable space includes a premises (e.g., house, building, factory, etc.) and in other embodiments the occupiable space includes a vehicle (e.g., car, truck, boat, plane, etc.). In this way, an occupiable space automation system, when used in a vehicle, can be used for climate control, power seats, windows, mirrors, entertainment systems, etc.

A system for occupiable space automation 100 includes a plurality of periphery devices 102(1)-102($n$) (which may be referred to generally as periphery devices 102 (e.g., sensor, user-activated element, a clock, and/or a timer) in an occupiable space 104 (e.g., premises, vehicle, etc.) and an occupiable space automation control system 106 (which may also be referred to as brain device (BD)) in electronic communication over a network 108 with the plurality of periphery devices 102. The plurality of periphery devices 102 is coupled with at least one controller 110 configured to electronically control operation of at least one occupiable space device 112 (which may also be referred to as a target device) (e.g., lights). The occupiable space automation control system 106 includes a server 114 (e.g., remote server, local device, etc.) and a database 116.

The occupiable space automation control system 106 further includes a neural network 118 of a plurality of artificial neurons 120$a$-120$n$ (which may be referred to generally as artificial neurons 120) interconnected by a plurality of synapses 122$a$-122$n$ (may be referred to generally as synapses 122). The plurality of artificial neurons 120 includes a device layer 124 associated with and configured to receive input from the plurality of periphery devices 102, and includes a context layer 126 configured to receive at least one signal indicative of context conditions, such as environmental (e.g., geolocation conditions) and/or temporal conditions. In certain embodiments, the plurality of artificial neurons 120 includes a complex connections layer 128 associated with recurrent connections of the context layer 126 and the device layer 124.

Each artificial neuron 120a-120n of the plurality of artificial neurons 120 comprises a neuron state and a neural input threshold value, and each artificial neuron 120a-120n is configured to receive a first neural input, to alter the neuron state when the first neural input received at the artificial neuron crosses the neural input threshold value, and to initiate at least one response event dependent on the neuron state. The at least one response event provides at least one second neural input to other artificial neurons 120a-120n of the plurality of artificial neurons 120. Each of the plurality of synapses 122 interconnects a different pair of artificial neurons 120a-120n, and comprises a coupling strength that varies depending on response events of the corresponding pair of artificial neurons within a predetermined time window. For example, the coupling strength at the first synapse 122a between the first artificial neuron 120a and the second artificial neuron 120b is less than the coupling strength at the second synapse 122b between the second artificial neuron 120b and the $n^{th}$ artificial neuron 120n. In certain embodiments, the coupling strength of at least one of the plurality of synapses 122 varies if response events of the corresponding pair of artificial neurons 120 are generated within the predetermined time window. In certain embodiments, the coupling strength of at least one of the plurality of synapses 122 varies if response events of the corresponding pair of artificial neurons 120 are not generated within the predetermined time window. In certain embodiments, at least one of the plurality of synapses 122 includes a coupling strength upper limit to require response events of the plurality of artificial neurons 120 to exceed the neural input threshold value for at least one of the plurality of artificial neurons 120. In certain embodiments, the occupiable space automation control system 106 is configured to alter the neuron state when the first neural input and the at least one second neural input exceed the neural input threshold value. In certain embodiments, the occupiable space automation control system 106 is configured to alter the neuron state when the first neural input and the at least one second neural input drop below the neural input threshold value.

The occupiable space automation control system 106 is configured to adaptively predict a predicted activity pattern of the plurality of periphery devices 102 based on response events of the plurality of artificial neurons 120 and coupling strengths of the plurality of synapses 122. The occupiable space automation control system 106 is configured to automatically operate the at least one controller 110 based on the predicted activity pattern. In certain embodiments, the occupiable space automation control system 106 is configured to automatically execute an operation upon detection of a deviation from the predicted activity pattern. In certain embodiments, the occupiable space automation control system 106 is configured to automatically operate the at least one controller 110 in response to electronic input received from at least one of the plurality of periphery devices 102. In certain embodiments, the occupiable space automation control system 106 is configured to receive a user override preventing the occupiable space automation control system 106 from automatically operating the at least one controller 110 based on the predicted activity pattern.

Figure 2:
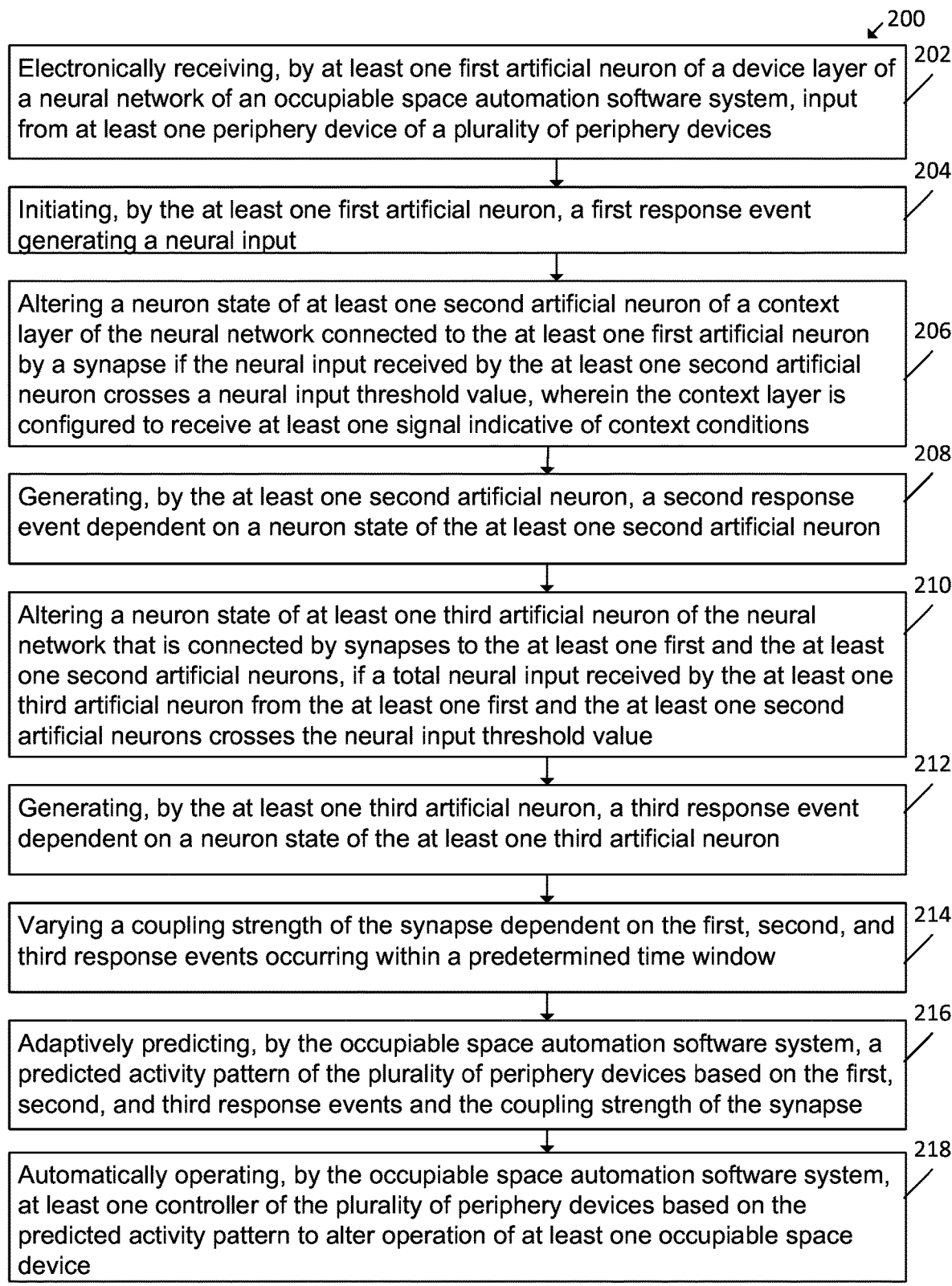
FIG. 2 is a flowchart illustrating steps of a method for occupiable space automation that may be implemented using the system of FIG. 1.

FIG. 2 is a flowchart illustrating processing steps 200 for occupiable space automation. In step 202, the method includes electronically receiving, by at least one first artificial neuron of a device layer of a neural network of an occupiable space automation control system, input from at least one periphery device of a plurality of periphery devices. In step 204, the method includes initiating, by the at least one first artificial neuron, a first response event generating a neural input. In step 206, the method includes altering a neuron state of at least one second artificial neuron of a context layer of the neural network connected to the at least one first artificial neuron by a synapse if the neural input received by the at least one second artificial neuron crosses a neural input threshold value, wherein the context layer is configured to receive at least one signal indicative of context conditions. In step 208, the method includes generating, by the at least one second artificial neuron, a second response event dependent on a neuron state of the at least one second artificial neuron. In step 210, the method includes altering a neuron state of at least one third artificial neuron of the neural network that is connected by synapses to the at least one first and the at least one second artificial neurons, if a total neural input received by the at least one third artificial neuron from the at least one first and the at least one second artificial neurons crosses the neural input threshold value. In step 212, the method includes generating, by the at least one third artificial neuron, a third response event dependent on a neuron state of the at least one third artificial neuron. In step 214, the method includes varying a coupling strength of the synapse dependent on the first, second, and third response events occurring within a predetermined time window. In step 216, the method includes adaptively predicting, by the occupiable space automation control system, a predicted activity pattern of the plurality of periphery devices based on the first, second, and third response events and the coupling strength of the synapse. In step 218, the method includes automatically operating, by the occupiable space automation control system, at least one controller of the plurality of periphery devices based on the predicted activity pattern to alter operation of at least one occupiable space device.

Neuron Activation and Threshold.

In certain embodiments, each neuron has a specific input threshold value that has to be exceeded to trigger transition of the neuron from an Off state to an On state. In other words, each neuron (which may also be referred to herein as a unit of the network) of the BD includes an activation threshold. Thus, transition occurs only if a sum of all the inputs to the neuron exceeds the threshold. Some neurons generate a single response event (which may be referred to herein as a spike) only at transition from an Off state to an On state. Other neurons generate a sequence of spikes as long as these neurons remain in an On state. Some neurons may generate a single spike at transition from an On state to an Off state. Finally, some neurons can generate a sequence of spike events as long as these neurons remain in an Off state.

Effect of Input on the Neurons.

In certain embodiments, all the neurons are connected with plastic (defined as capable of changing its strength) coupling elements (which may be referred to herein as synapses). In certain embodiments, a synapse can be positive (excitatory) or negative (inhibitory). Thus, if two neurons A and B are connected by synapse $G_{ba}$ from A to B, then a spike in neuron A will bring neuron B closer to its activation threshold if $G_{ba}>0$ (excitatory synapse), or farther from the threshold if $G_{ba}<0$ (inhibitory synapse). This effect of neuron A on neuron B decays over time.

Figures 3A, 3B:
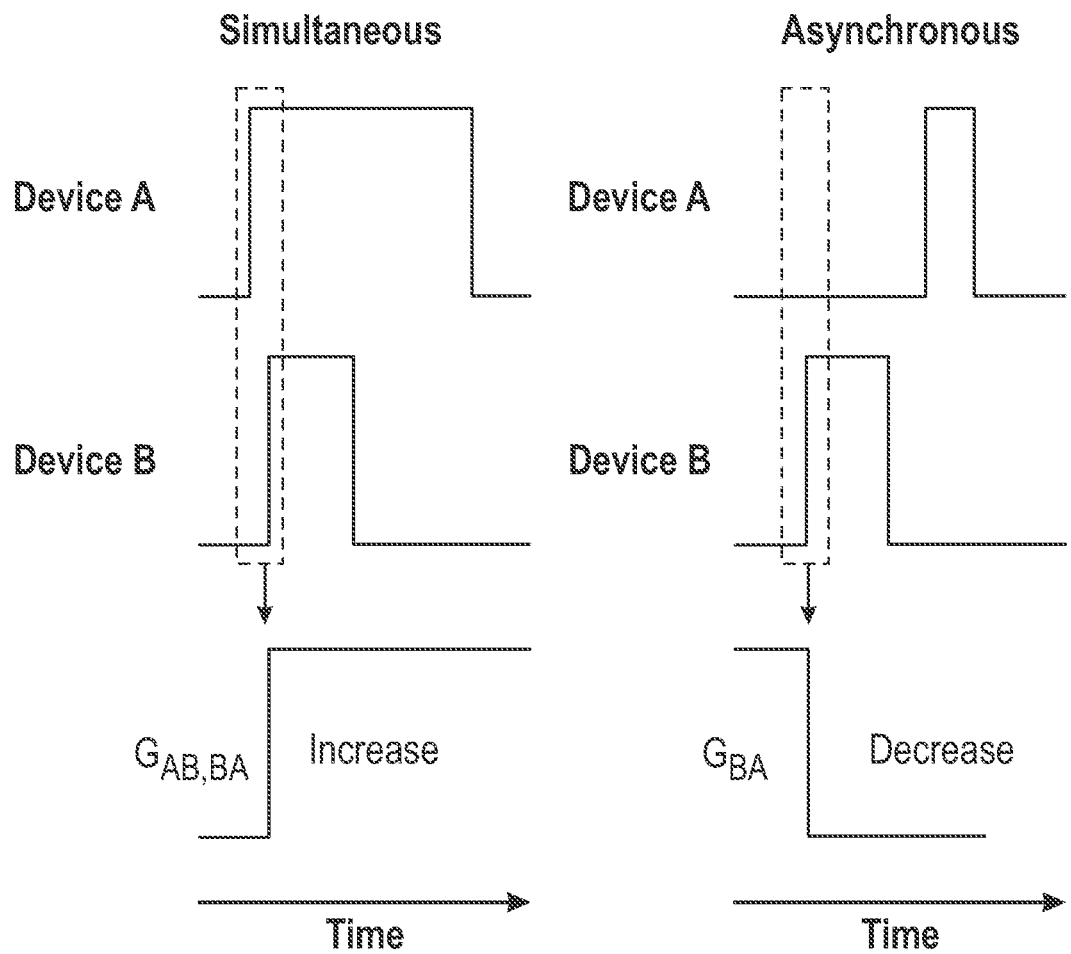
FIG. 3A is a diagram illustrating plasticity of connections between neurons of the occupiable space automation system of FIG. 1 depending upon simultaneous activity between two periphery devices.
FIG. 3B is a diagram illustrating plasticity of connections between neurons of the occupiable space automation system of FIG. 1 depending upon asynchronous activity between two periphery devices.

FIGS. 3A and 3B are diagrams illustrating plasticity of connections between neurons of a brain device (BD) depending upon simultaneous and/or asynchronous activity between two periphery devices. In other words, FIGS. 3A and 3B illustrate effects of input on the neurons.

Plasticity of Connections: Increase of Coupling.

Referring to FIG. 3A, in certain embodiments, any synaptic connection $G_{ba}$ is plastic, so it can increase or decrease its value depending on the history of device activation (described in more detail below). Specifically, if two devices, device A and device B, both spike (e.g., both switch to On state) within specific time window, then $G_{ba}$ and $G_{ab}$ both increase by predetermined value $\alpha$. The value of $\alpha$ determines the rate of learning. The same idea is applied to any number of devices: A, B, C, . . . . If all of them spike within a certain time window, then synapses between all devices increase their strength.

Plasticity of Connections: Decrease of Coupling.

Referring to FIG. 3B, to constrain training to only sensible connections, the BD utilizes a rule that synaptic connections $G_{ba}$ from device A to device B should decrease if device B spikes (e.g., switch to On state) without a corresponding (within a time window) spike in device A. For example, if wall switch B is activated without activation of the motion sensor A, then connection from A to B, $G_{ba}$, will decrease by the discounting value $\beta$ that depends on the state of the system. The same idea is generalized to any number of devices: A, B, C, . . . . If some of them spike and some do not spike within a certain time window, then connection from spiking to non-spiking devices will decrease. This will let the BD discard, get rid of, or otherwise ignore non-representative connections, e.g., between motion sensors and functionally unrelated switches in another part of the occupiable space.

As an example of how these rules may work between two units A and B, assume A is a "sensing" device (motion sensor, contact sensor, etc.) (which may be referred to as a periphery device) and B is a controller (e.g., a wall switch, but it can be any other device controlling anything in the occupiable space environment). Synapse $G_{ba}^{y}$, connecting A to B, will increase its value if activation of A (e.g., user triggers motion sensor event) coincides within some time window with activation of B (e.g., user triggers a wall light switch) then the strength of connections from A to B will increase. Eventually an A→B connection reaches the value exceeding the threshold for B activation, so the motion sensor activation will trigger a switch response without a user actually touching the switch, resulting in a system learned association. If, however, controller B is triggered by a user without activating motion sensor A, then it would suggest that motion sensor A is not relevant for controller B and connection $G_{ba}$ from A→B will decrease.

Limitation on the Total Input Strength.

In certain embodiments, the BD includes a rule limiting the strength of the total synaptic input to any neuron. If N other neurons (A1, A2, . . . , An) representing any devices or any other elements of the system project to a neuron B (e.g., representing light switch), then the total synaptic strength of all these connections, $\Sigma G_n$, is limited by a value that is specific to neuron B and established in respect to the threshold of activation of the neuron B. This requires activation of a few input devices (input neurons) simultaneously to activate the target device. For example, assume switch B is typically activated when motion sensor A1 is activated and door contact sensor A2 is activated. Then this rule limits each of the synapses A1→B and A2→B, such that both of them (A1 and A2) should be activated simultaneously to activate device B. This rule is applied to any number or type of presynaptic neurons. This is an important rule that allows the system to learn that a specific device should only be activated under specific conditions.

Other Considerations.

The described learning rules are not restricted to "sensing device—controller" pairs only. Rather, synaptic connections can be formed according to the same mechanism between other types of devices. The links are likely to appear in "controller—controller" pairs, which a user typically activates simultaneously or within a short time window (e.g., outside front door light and front yard light; room light and light in adjoining hall, etc.). Moreover, the BD network may include multiple additional intermediate layers of units, and the same learning paradigm is used for connections between any of these units. Hence, the proposed synaptic modification rules may be universal for all the neurons in the BD. Though, in certain embodiments, a set of modifying synapses (affected by learning) may be restricted for certain types of devices only, depending on particular implementation of the occupiable space automation system and specific preferences of the user.

The above system architecture and features can establish the necessary associations between neurons, and as explained in more detail below can be activated according to specific conditions (e.g., day of time, weather, etc.). For example, while it may be desirable for a typical household to turn bedroom lights On based on motion sensor activation at 8 pm, it will be very undesirable if the same would occur at 2 pm, wasting energy, or at 2 am, when somebody may be sleeping in the room. Therefore, those associations should be conditional and based on typical pattern of user behaviors, as described in more detail below.

State Neurons to Implement Environmental Factors.

The BD includes additional layers of neurons referred to as state neurons to account for any dependencies on the state of the world or a history of the system's operations, such as time of the day, weather (e.g., sunny, rainy, etc.), season (e.g., winter, summer, etc.), day of the week (e.g., weekends, work days, etc.), occupant calendars and geolocations, history of activity, etc. A state neuron will always be active when a certain environment and/or temporal condition is fulfilled. For example, to take into account time of day, the BD may include a layer of time neurons (T1, . . . , Tn) where each neuron is active (i.e., generates a sequence of spikes) during specific time window. For example, time neuron T1 may be active from 1 pm until 4 pm, T2 is active from 2 pm until 5 pm, etc. The length of the time window can vary depending on specific needs.

Figure 4:
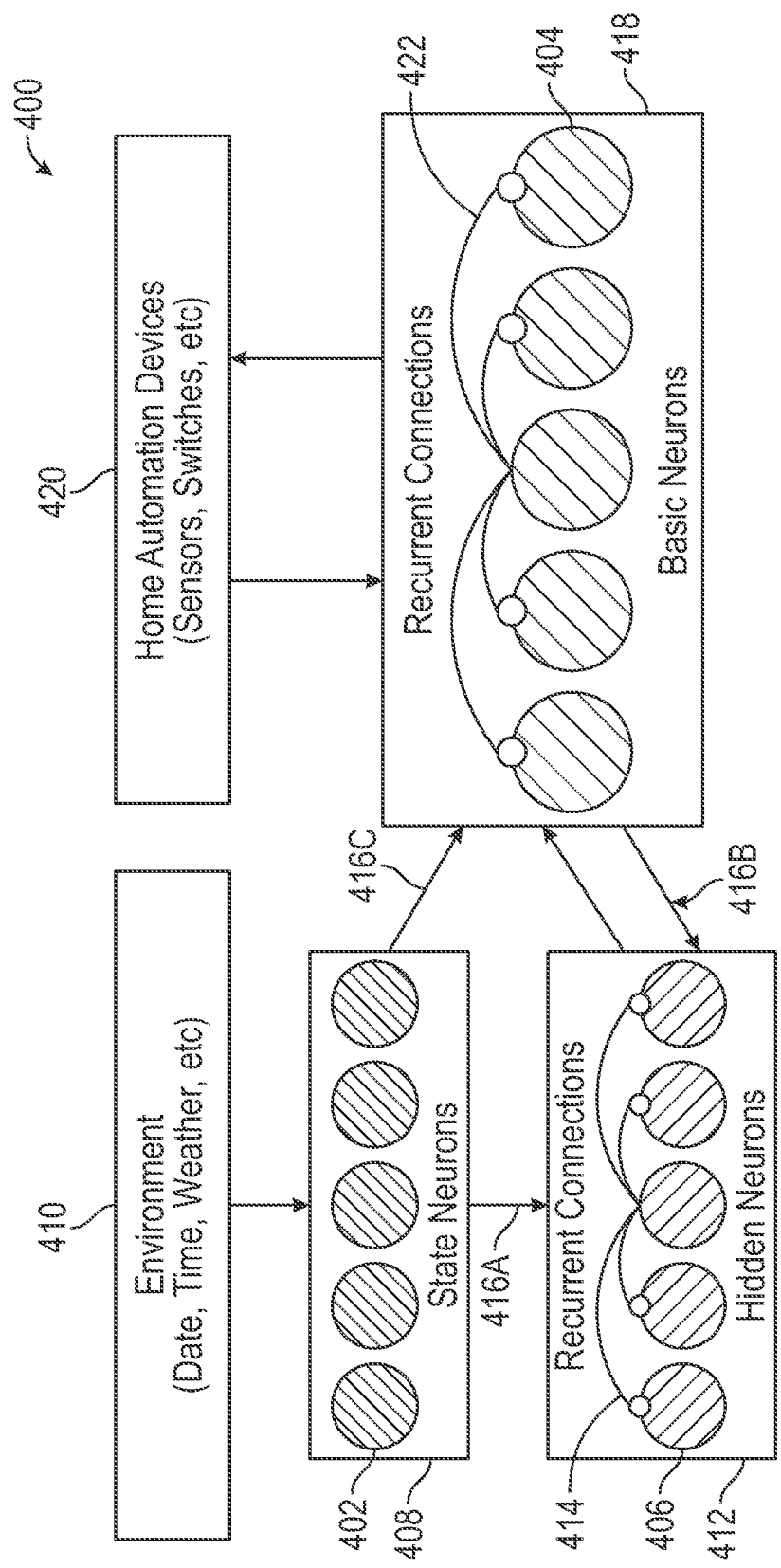
FIG. 4 is a schematic diagram illustrating system architecture according to one implementation of the occupiable space automation system of FIG. 1, including state neurons, basic neurons, and hidden neurons.

FIG. 4 is a system diagram 400 of the occupiable space automation system 100 of FIG. 1 including state neurons 402, basic neurons 404, and hidden neurons 406. In particular, the BD comprises several layers of artificial neurons. Activity of the state neurons 402 of the state neuron layer 408 reflect environment and/or temporal conditions 410, which include daytime, weather, and/or season, etc., which may be electronically received from sensors, geolocation data, calendar, and/or clock, etc. Environmental conditions 410 may also include geolocation conditions, such as whether occupants and/or users are present in the occupiable space (e.g., is the space occupied, who occupies the space, etc.).

The hidden layers 412 include hidden neurons 406, which have recurrent intralayer connections 414 and interlayer connections 416A, 416B. For example, the hidden neurons 406 can communicate with the state neurons 402 via interlayer connections 416A (e.g., receive unilateral communication). The hidden neurons are aimed at performing complex associations and generalizations based on the input from the state neurons 402 and from the device specific neurons 404 (which may also be referred to herein as basic neurons). The device specific layer 418 of device specific neurons 404 includes neurons associated with specific occupiable space automation devices 420. These device specific neurons 404 interact with hidden neurons 406 and also directly communicate to each other 422. Further, these device specific neurons 404 can communicate with the state neurons 402 via interlayer connections 416C (e.g., receive unilateral communication) and/or communicate with the hidden neurons 406 via interlayer connections 416B (e.g., bilateral). Finally, device specific neurons interact with a layer of PDs (e.g., sensors, switches, thermostats, lights, appliances, etc.) to control and to reflect state of these devices.

During an initial training phase, a user operates (directly by manual operation or indirectly by sensory activity) the PDs, which provides input to the system (from the layer of physical devices to the layer of device specific neurons). Thus, for example, when a user triggers a motion sensor in a living room, the state of the associated device specific neuron A changes from Off to On. If a user then turns On a light switch in the living room, the state of associated device specific neuron B changes from Off to On. Another input to the BD is represented by the state neurons. For example, when the action occurs within the time window and when the state neuron T1 (representing that specific time window) is active (spiking), the input from T1 is sent to the BD. During the training phase, the network forms user specific connections between all these units. For example, the BD learns that activity in A during the time window defined by T1 which usually leads to activation of B: A+T1→B.

After initial training, during a normal operation phase, the input to the system still includes input from layers of the physical devices and state neurons. However, based on the internal connections between state, hidden, and basic neurons formed during training, the system now predicts activity of the physical layer devices. This creates the output from BD to the PDs that controls the state of these PDs. So, for example, after training the system would predict that simultaneous activation of the motion sensor A and the time neuron T1 should lead to turning On the light switch B, and would execute this operation without a need for end user to turn light switch On manually.

Multiple Layers of State Neurons.

Different conditions can be implemented simultaneously by using different groups of state neurons. For example, in one embodiment, the BD includes a layer of state neurons representing time of day and another layer of state neurons representing months (January-December). This will allow the BD to learn activating specific PDs only if all the conditions are fulfilled (e.g., time is 3-5 pm and it is summer). The type of state neurons that can be introduced is not limited. Essentially any conditions (e.g., environment, history of events, etc.) can be represented by state neurons. For example, state neurons may represent select weather (e.g., rain, snow, clear), type of device based on typical duration of device activation (e.g., distinct devices activated every day for long time, such as porch light and devices activated for short time based on motion sensor activation), etc.

During learning, all state neurons can change connections to any of the other neurons. Note that for these synaptic connections the same set of modification rules, as described above, can be used. In certain embodiments, limiting the total input strength (as described above) is important as it introduces associations between, for example, a group of sensors and a group of state neurons, so the target occupiable space device will be activated only when several conditions are fulfilled simultaneously.

Receptive Fields of State Neurons.

Since different physical devices may be operated by a user in different environmental and/or temporal conditions (e.g., some devices may be activated during specific time window and other at any time), the state neurons will form device and user specific "receptive fields"—the window of conditions (e.g., time window) when BD should turn target device On based on the other devices activity. For example, switch B is typically activated when motion sensor A is active and such activation only happens during specific time of day when time neuron T1 is active. Then limiting the total input strength limits each of the synapses A→B and T1→B, such that both of neurons (A and T1) should be active simultaneously to activate device B.

The receptive field is not limited by time but may be applied to any type of environmental conditions, and may be applied to any number of presynaptic neurons (e.g., it can be a combination of motion sensors, time neurons, "summer" neuron, "rain" neurons, etc.). This allows the system to learn that specific devices should be only activated under specific conditions (e.g., motion, time of the day, weather, season, etc.).

Figure 5A:
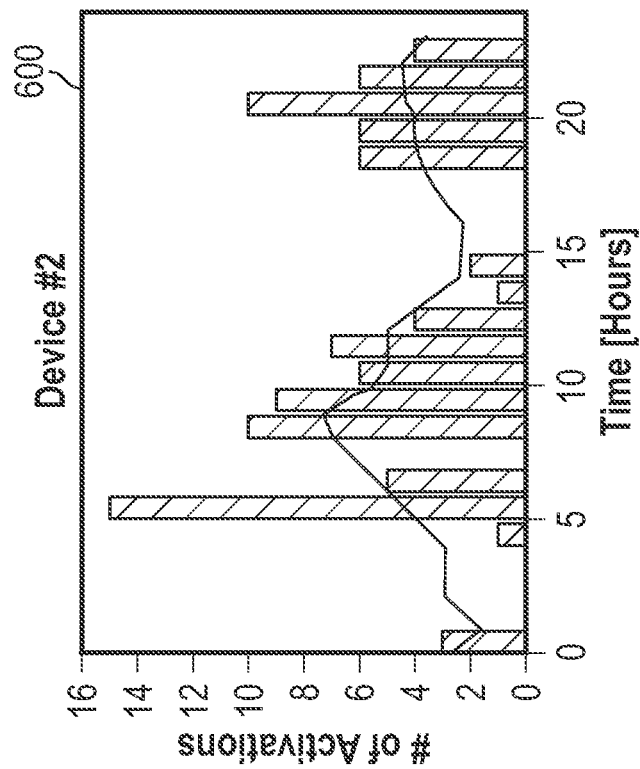
FIG. 5A is a histogram plotting the number of activations versus time illustrating receipt by a target device of connections from basic and time neurons by the occupiable space automation system of FIG. 1, for a first target device activated by a sensor device.

FIGS. 5A-6B are diagrams illustrating use of time neurons by the occupiable space automation system 100 of FIG. 1 by comparing two target devices (which may also be referred to as occupiable space devices) that are each activated by another device (e.g., periphery device). In particular, FIGS. 5A-6B illustrate a basic idea of receptive fields, using time neurons as an example. FIGS. 5A and 6A show two target devices (i.e., a first target device in FIG. 5A and a second target device in FIG. 6B) that are activated by another device (e.g., a sensor). Referring to FIG. 5A, illustrated is a histogram 500 of activation times for the first target device. The histogram 500 shows a specific time window 502 (e.g., 16-21 hours) during which the first device was typically activated. Referring to FIG. 5B, in this case, the BD identified a subset of time neurons 504 that formed positive excitatory (activating) connections to the device neuron 506 by activation of the sensor neuron 508. As a result, a sensor device can activate the first target device during specific time window only (e.g., 16-21 hours).

Figure 6A:
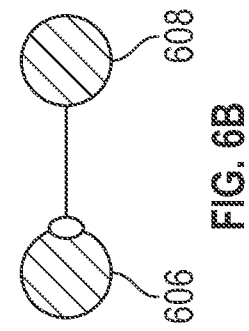
FIG. 6A is a histogram plotting the number of activations versus time illustrating receipt by a target device of connections from basic neurons by the occupiable space automation system of FIG. 1, for a second target device activated by a sensor device.
Figure 5B:
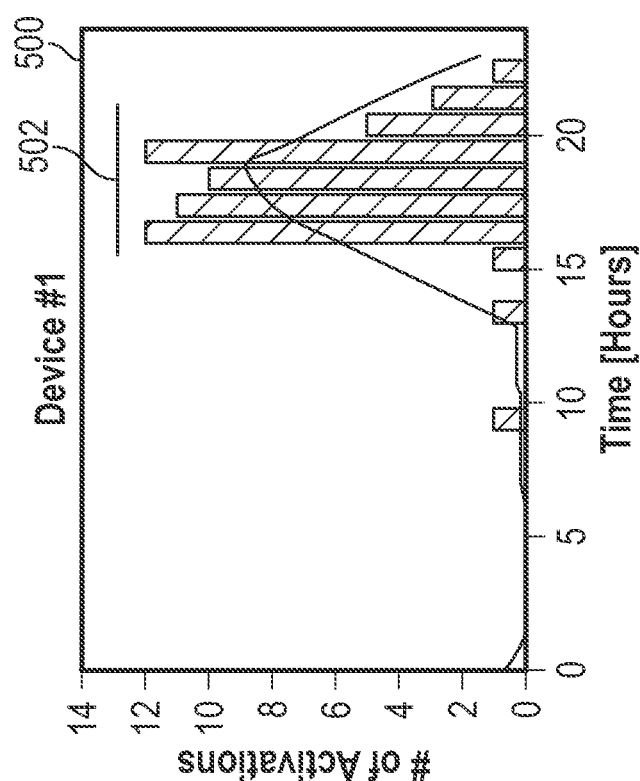
FIG. 5B is a diagram illustrating identification by the occupiable space automation system of FIG. 1 of a subset of time neurons so that a sensor device can activate the first target device during a specific time window only.
Figure 6B:
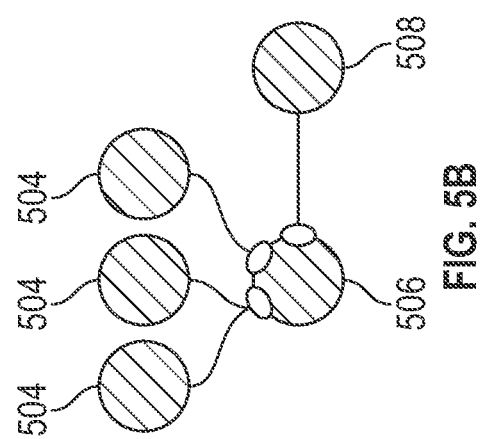
FIG. 6B is a diagram illustrating a lack of identification by the occupiable space automation system of FIG. 1 of a subset of time neurons so that a sensor device can activate the first target device at any time.

FIG. 6A represents another example in histogram 600 when the activation times of the second target device are distributed almost uniformly in time, showing that the user does not have any time preference for the second target device activation. Referring to FIG. 6B, in this case no connections from time neurons were trained, and a sensor device can switch that device On at any time when a sensor neuron 608 with a positive excitatory connection to the device neuron 606 is activated.

Multiple Receptive Fields of State Neurons.

Figure 7:
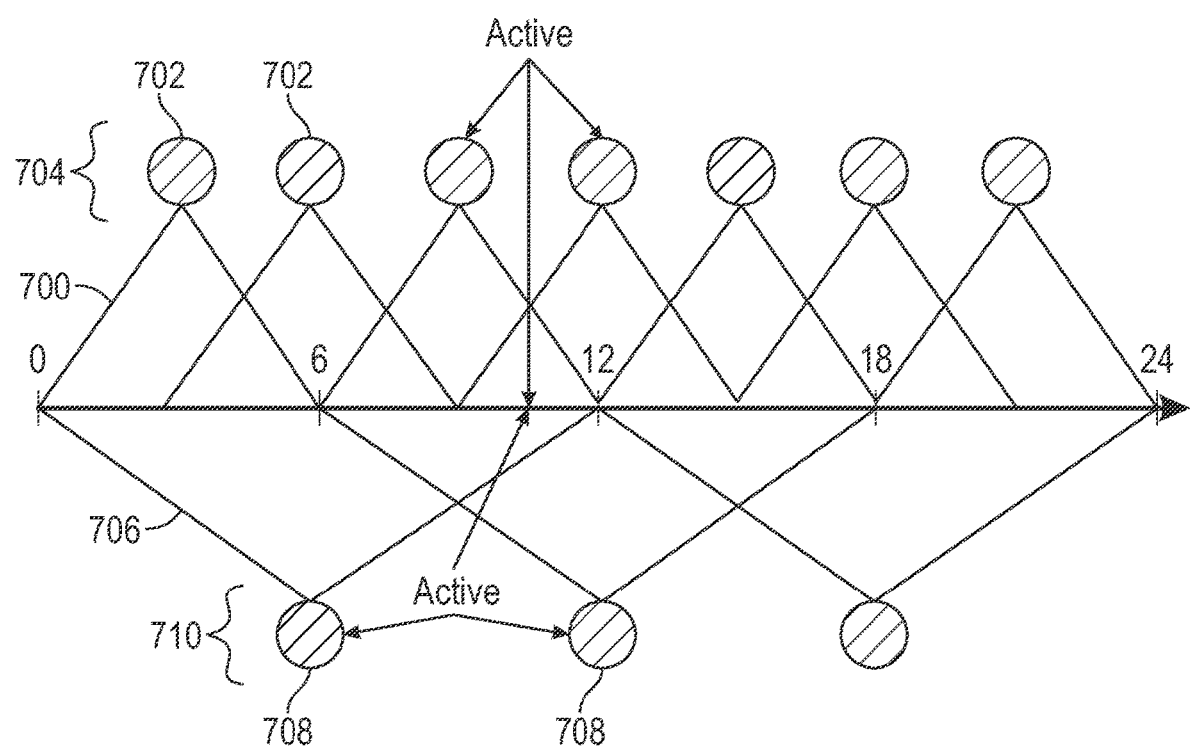
FIG. 7 is a diagram illustrating a two-layer implementation of time neurons for the occupiable space automation system of FIG. 1.

In certain embodiments, many overlapping layers of neurons are considered for each specific type of environmental conditions (e.g., time), where different layers are characterized by different widths of associated conditions (e.g., time windows). FIG. 7 is a diagram illustrating a two-layer implementation of time neurons. The diagram illustrates an example of the two-layer implementation of time neurons, with a first receptive field 700 of 6 hours (3+/−3 hours) for the neurons 702 in the first layer 704 and a second receptive field 706 of 12 hours (6+/−6 hours) for the neurons 708 in the second layer 710. Each neuron inside a given layer has its own unique number, which determines a center of the receptive field 700, 706. These receptive fields 700, 706 overlap to allow more precise identification of the operational conditions for a physical device.

Continuous Training when Target Device is on.

The continuous On state of the PD represents important information since it indicates that a user wants to keep it On under specific conditions. This information may potentially be as important as the information associated with the event of explicit turning a device On by user. To take into account this additional information, in certain embodiments, each device specific neuron may generate spikes spontaneously (randomly or periodically) when an associated device stays On, in addition to when a user turns it On. Since time neurons are active within a specific time window, all the time neurons active during a time when a light remains On will be trained (i.e., the system will establish links between these time neurons and the device specific neuron). This may be particularly useful for devices that are expected to stay On for long periods of time, e.g., porch light.

Conditions to Turn Device Off Based on the State of the Network.

When a device specific neuron B is switched to its active state, it enforces a corresponding device to stay On (e.g., light stays On). The device then stays in the On state (and therefore the light remains On) for a duration of time controlled by (a) dynamics of device specific neuron B (explained in more detail below), and/or (b) "decay" of inputs from those neurons that triggered activation of B: (A1, A2, . . . , T1, T2, . . . )→B. These synaptic inputs may decay with different time constants, e.g., $\tau_1 < \tau_2 < \ldots < \tau_N$, depending on the type of the device and/or history of activation. Decay of input from any neuron may be governed by one or many time constants. For example, the target device B may switch Off when the sum of all the inputs to that device decreases below a threshold value that is specific to this device. This threshold may be the same or different from the activation threshold (see above).

Figure 8:
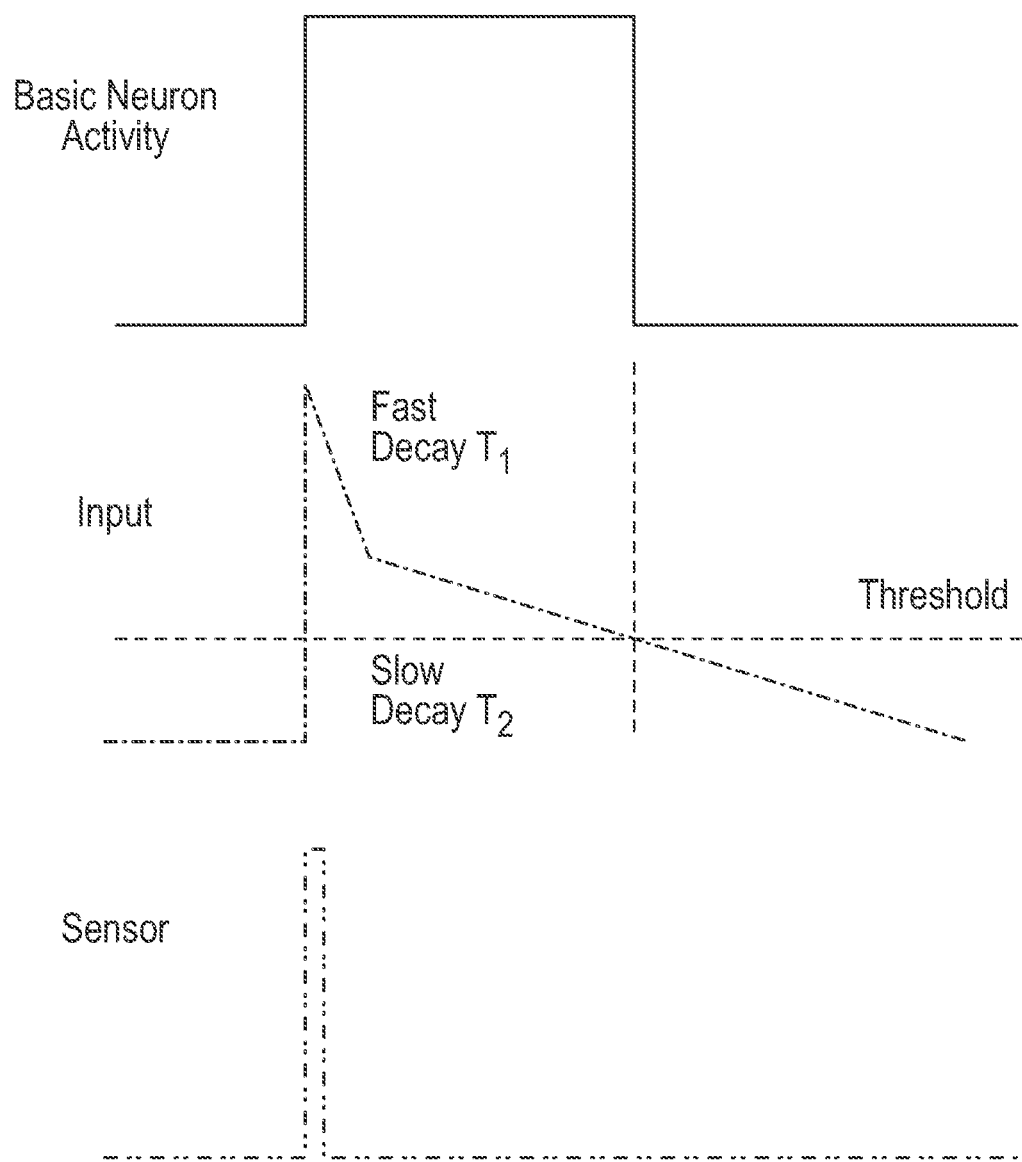
FIG. 8 is a diagram illustrating decay of inputs of a device specific neuron from those neurons that triggered activation of the device specific neuron for the occupiable space automation system of FIG. 1.

FIG. 8 is a diagram illustrating decay of inputs of a device specific neuron from those neurons that triggered activation of the device specific neuron. In certain embodiments, the BD incorporates two, fast and slow, decay time constants, $\tau_1 < \tau_2$, for inputs from each physicals device: $S_1 e^{-t/\tau_1} + S_2 e^{-t/\tau_2}$. FIG. 8 shows an example of such inputs decaying with different time constants. A constant input ($\tau_3 = \infty$) from a state neuron: $S_3$ may also be implemented. The strength of the inputs may be set such that $S_1 + S_2 > S_{th}$, $S_2 < S_{th}$, $S_2 + S_3 > S_{th}$, $S_3 < S_{th}$, where $S_{th}$ is the threshold for turning this device Off. In the first example, light switch B is activated by the input from a single device (motion sensor A) alone in the closet where time is irrelevant, hence there are no inputs from time neurons. Then device B switches to the Off state after a short time, with time constant $\tau_1$. This happens because the fast component decays quickly with time constant $\tau_1$, and a slow component alone is not sufficient to keep input above the threshold: $S_2 < S_{th}$. In another example, in the family room, the light is triggered On by motion sensor A only during a specific time window, defined by time neuron T1. Then additional input from the time neuron is established during training. In that case, the device neuron B stays On until both components of the input from A (fast $\tau_1$, and slow $\tau_2$) would decay. This happens because even after a fast component decays, a remaining slow component of the input from A and constant input from time neuron T1 together are sufficient to keep the total input above the threshold: $S_2 + S_3 > S_{th}$. Hence, the device specific neuron would remain active longer, until slow component decay with time constant $\tau_2$. Then the light would go Off since remaining input from the time neuron alone is not sufficient: $S_3 < S_{th}$. The same algorithm can be applied for any number of time constants.

It is also possible to introduce a gradual scale for device activity in the interval $[\tau_1, \tau_2]$. Based on typical device activity (e.g. typical duration of device activity recorded in the log), the input from time neurons can be rescaled such that a stronger input (in case of long period of typical device activity) produces a longer time before a network-induced switch-off event.

This is only one possible example of complex dynamics caused by different timescales of the synaptic input. Generally, this approach allows constructing different activation-inactivation schemes for smart control of a device's activity duration.

Conditions to Turn Device Off Based on the History of User Based Operation.

In certain embodiments, in another version of having conditions to turn the device off based on the state of the network, the BD may keep a PDs active for a specific duration of time based on the history of the PDs past activity. Thus, during the training phase, the information about how long a user typically keeps On a specific device B is stored and then is used to define how long the BD would keep that device On. Different rules can be applied (e.g., based on median duration of device activity in the history log). This approach selects a specific duration of time for PDs to be On. Therefore, for example, a closet or bathroom light will go Off in just few minutes after activation, while a family room light will stay On for a longer time.

User Based Override.

In certain embodiments, the BD includes a user-based blockage (or override) of the BD control. For example, if a light is turned On by BD but then it is turned Off by user within specific time window, the BD will ignore neural network control for specific time (Tblock1). This will prevent the system from turning a light On when user decided that it should be Off under specific circumstances (e.g., watching movie in the movie theater). The blockage time may be further increased based on a particular algorithm if this situation repeats. Similarly, if a light is turned off by the BD but then user turns it On again within specific time window (Twait), then the BD will ignore neural network control for a specific time (Tblock2). This will prevent system from turning a light Off when user decided that it should be On under specific circumstances (e.g., user is in the room but outside direct view of the motion sensor). In certain embodiments, a user-based override can use manual control (e.g., a switch) or voice control (e.g., a commercially available voice recognition system such as Amazon Alexa).

Unlearning Rules.

The BD can unlearn previously learned rules to allow the system to change learned rules, such as to account for sunrise/sunset seasonal time shift, changes in user habits, or other factors. In certain embodiments, unlearning may be implemented by decreasing synaptic weights based on user interference, such as by implementing the following steps:

a. A synaptic strength is decreased based on the interference. Thus, if during a normal operation phase, activation of a group of neurons (A1, A2, . . . , T1, T2, . . . ) triggers activation of device B because it was previously learned as a useful rule, (A1, A2 . . . T1, T2 ... )→B, but then a user manually overrides this rule by switching Off device B, it will trigger decrease of synaptic weights for all synapses of all the neurons (devices or state) formed projections to B: (A1, A2 ... T1, T2 ... )→B.

b. To ensure that a "useful" link would not fall below activation threshold just because it is manually overridden by user in a few special cases (that would always occur in the real environment), a slow positive learning may be continued even during a normal operation phase. Thus, even after a combination of the inputs becomes sufficiently strong to trigger activation of the target device B: (A1, A2 ..., T1, T2 ... )→B, so the BD starts controlling device B—normal operation phase, the learning will continue. Each time the BD switches device B On based on the combination of the inputs (A1, A2 ... T1, T2 ... ) as described above, some (e.g., smaller than during initial training) synaptic weight increase from all the devices (A1, A2 ... T1, T2 ... ) to B is implemented, similar to what occurred during the initial training phase.

c. In such implementation, initial training would quickly increase synaptic links for the useful connections, so the BD will start controlling light (e.g., turning a light On if several presynaptic devices are activated simultaneously as described above). If there is no cancellation of the BD trigged event by the user, it will further increase synaptic weights in small increments until the maximum strength per device (Wmax) is attained. However, each time when the user turns the device Off manually, such action will decrease the weight. If this only happens once in a while, it will not lead to the termination of a link between devices since many small increases of the weight when BD turns device On correctly will overcome the effect of a few events when the connection is based on the user override. However, consistency with turning a device Off manually by a user to overcome BD decision (as it may be for light turning On too early after sunrise/sunset time shift) will eventually bring this connection below the threshold. As a result, this connection will fall below the threshold and will be unlearned.

Possible 'Soft Learning' Implementation.

In certain embodiments, slow, soft switching between the states of the control devices (like slow dimming on and off lights, instead of turning it on and off instantly) allows time for the user to react to correct the device state change. To implement dimming, the state of the single device can be represented by multiple neurons responsible for different levels of activations of the particular device—like different light levels or temperature.

In certain embodiments, a proposed system can be implemented as standalone software running either locally (by a user) or remotely (by a provider). In both cases, the training phase can be implemented (a) in real time, thus the running software interacts with occupiable space controller (such as ISY or SmartThings hub) to get input about events; after a sufficient period of training when associations (synaptic links) are established, the system starts providing signals to control PDs; (b) off line, using previously saved logs of user activity over certain period of time. In that case, the BD software may be trained on a logged file to establish links and then is immediately ready to control PDs. As discussed above, a neural network-based system for smart occupiable space automation performs learning and adaptation based on a user's behavior. As a result of learning, the neural network acts as an artificial intelligence system, which controls occupiable space automation devices in a way that mimics typical user behavior. The system requires a relatively short learning period and a small number of training cases for successful operation.

Figure 9:
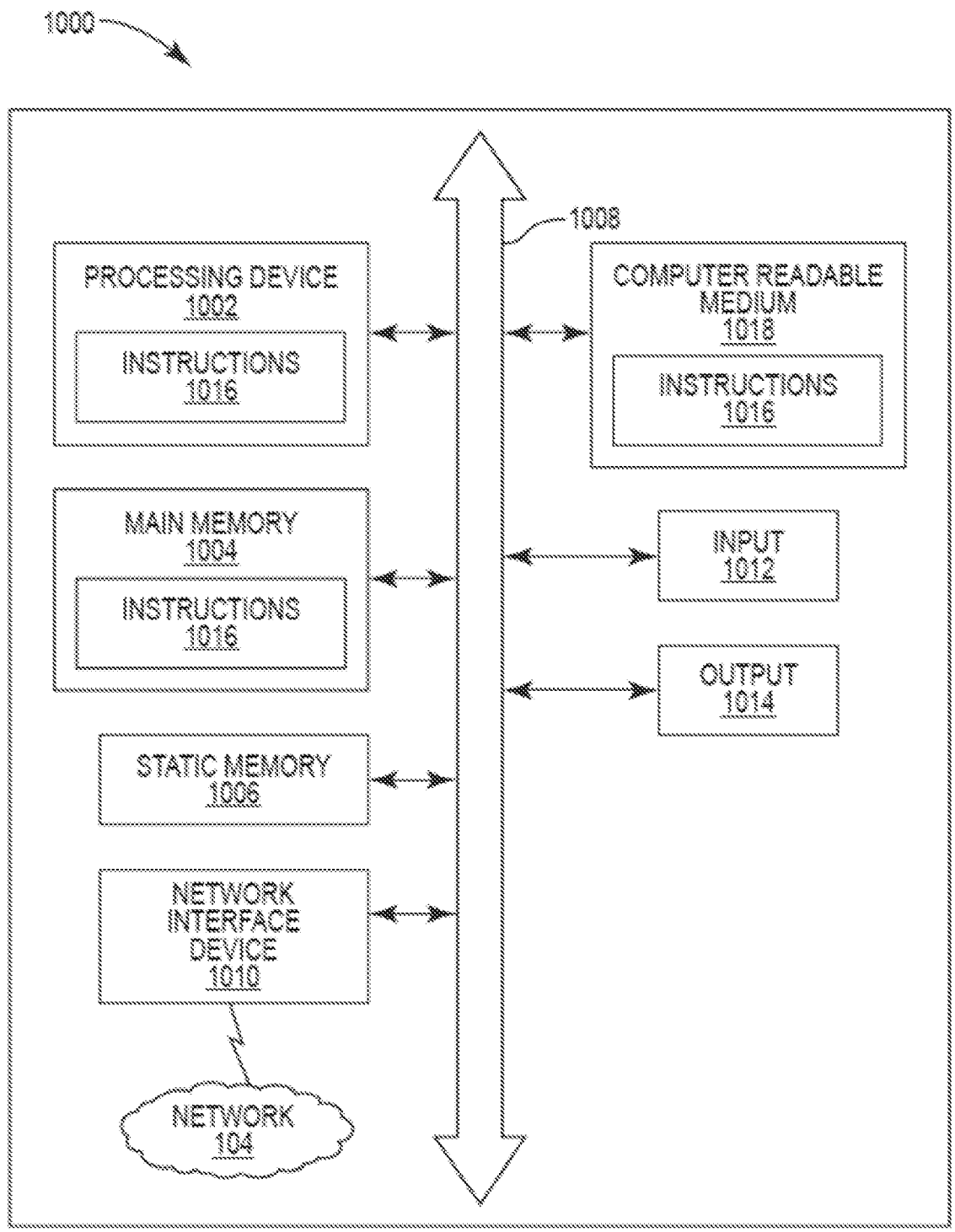
FIG. 9 a schematic diagram of a generalized representation of a computer system that can be included in any one or more components of the occupiable space automation system of FIGS. 1-8.

FIG. 9 is a schematic diagram of a generalized representation of a computer system 1000 that can be included in any one or more components of the occupiable space automation system of FIGS. 1-8. In this regard, the computer system 1000 is configured to execute instructions from a computer-readable medium to perform these and/or any of the functions or processing described herein.

In this regard, the computer system 1000 may include a set of instructions that may be executed to program and configure programmable digital signal processing circuits for supporting scaling of supported communications services. The computer system 1000 may be connected (e.g., networked) to other machines in a LAN, an intranet, an extranet, or the Internet. While only a single device is illustrated, the term "device" shall also be interpreted to include any collection of devices that individually or jointly execute a set (or multiple sets) of instructions to perform any one or more of the methodologies discussed herein. The computer system 1000 may be a circuit or circuits included in an electronic board card, such as a printed circuit board (PCB), a server, a personal computer, a desktop computer, a laptop computer, a personal digital assistant (PDA), a computing pad, a mobile device, or any other device, and may represent, for example, a server or a user's computer.

The computer system 1000 in the illustrated embodiment includes a processing device or processor 1002, a main memory 1004 (e.g., read-only memory (ROM), flash memory, dynamic random access memory (DRAM), such as synchronous DRAM (SDRAM), etc.), and a static memory 1006 (e.g., flash memory, static random access memory (SRAM), etc.), which may communicate with each other via a data bus 1008. Alternatively, the processing device 1002 may be connected to the main memory 1004 and/or static memory 1006 directly or via some other connectivity means. The processing device 1002 may be a controller, and the main memory 1004 or static memory 1006 may be any type of memory.

The processing device 1002 represents one or more general-purpose processing devices, such as a microprocessor, central processing unit, or the like. More particularly, the processing device 1002 may be a complex instruction set computing (CISC) microprocessor, a reduced instruction set computing (RISC) microprocessor, a very long instruction word (VLIW) microprocessor, a processor implementing other instruction sets, or other processors implementing a combination of instruction sets. The processing device 1002 is configured to execute processing logic in instructions for performing the operations and steps discussed herein.

The computer system 1000 may further include a network interface device 1010. The computer system 1000 may optionally include an input 1012, configured to receive input and selections to be communicated to the computer system 1000 when executing instructions. The computer system 1000 may optionally include an output 1014, including but not limited to a display, a video display unit (e.g., a liquid crystal display (LCD) or a cathode ray tube (CRT)), an alphanumeric input device (e.g., a keyboard), and/or a cursor control device (e.g., a mouse).

The computer system 1000 may optionally include a data storage device that includes instructions 1016 stored in a computer readable medium 1018. The instructions 1016 may also reside, completely or at least partially, within the main memory 1004 and/or within the processing device 1002 during execution thereof by the computer system 1000, the main memory 1004 and the processing device 1002 also constitute computer readable medium. The instructions 1016 may further be transmitted or received over a network 104 via the network interface device 1010.

While the computer readable medium 1018 is shown in an embodiment to be a single medium, the term "computer-readable medium" should be interpreted to include a single medium or multiple media (e.g., a centralized or distributed database, and/or associated caches and servers) that store the one or more sets of instructions. The term "computer readable medium" shall also be interpreted to include any medium that is capable of storing, encoding, or carrying a set of instructions for execution by the processing device and that cause the processing device to perform any one or more of the methodologies of the embodiments disclosed herein. The term "computer readable medium" shall accordingly be interpreted to include, but not be limited to, solid-state memories, optical medium, and magnetic medium.

The embodiments disclosed herein include various steps. The steps of the embodiments disclosed herein may be formed by hardware components or may be embodied in machine-executable instructions, which may be used to cause a general-purpose or special-purpose processor programmed with the instructions to perform the steps. Alternatively, the steps may be performed by a combination of hardware and software.

The embodiments disclosed herein may be provided as a computer program product, or software, that may include a machine-readable medium (or computer readable medium) having stored thereon instructions which may be used to program a computer system (or other electronic devices) to perform a process according to the embodiments disclosed herein. A machine-readable medium includes any mechanism for storing or transmitting information in a form readable by a machine (e.g., a computer). For example, a machine-readable medium includes: a machine-readable storage medium (e.g., ROM, random access memory ("RAM"), a magnetic disk storage medium, an optical storage medium, flash memory devices, etc.); and the like.

Unless specifically stated otherwise and as apparent from the previous discussion, it is appreciated that throughout the description, discussions utilizing terms such as "processing," "computing," "determining," "displaying," or the like, refer to the action and processes of a computer system, or a similar electronic computing device, that manipulates and transforms data and memories represented as physical (electronic) quantities within the computer system's registers into other data similarly represented as physical quantities within the computer system memories or registers or other such information storage, transmission, or display devices.

The algorithms and displays presented herein are not inherently related to any particular computer or other apparatus. Various systems may be used with programs in accordance with the teachings herein, or it may prove convenient to construct more specialized apparatuses to perform the required method steps. The required structure for a variety of these systems is disclosed in the description above. In addition, the embodiments described herein are not described with reference to any particular programming language. It will be appreciated that a variety of programming languages may be used to implement the teachings of the embodiments as described herein.

Those of skill in the art will further appreciate that the various illustrative logical blocks, modules, circuits, and algorithms described in connection with the embodiments disclosed herein may be implemented as electronic hardware, instructions stored in memory or in another computer readable medium and executed by a processor or other processing device, or combinations of both. The components of the system described herein may be employed in any circuit, hardware component, integrated circuit (IC), or IC chip, as examples. Memory disclosed herein may be any type and size of memory and may be configured to store any type of information desired. To clearly illustrate this interchangeability, various illustrative components, blocks, modules, circuits, and steps have been described above generally in terms of their functionality. How such functionality is implemented depends on the particular application, design choices, and/or design constraints imposed on the overall system. Skilled artisans may implement the described functionality in varying ways for each particular application, but such implementation decisions should not be interpreted as causing a departure from the scope of the present embodiments.

The various illustrative logical blocks, modules, and circuits described in connection with the embodiments disclosed herein may be implemented or performed with a processor, a Digital Signal Processor (DSP), an Application Specific Integrated Circuit (ASIC), a Field Programmable Gate Array (FPGA), or other programmable logic device, a discrete gate or transistor logic, discrete hardware components, or any combination thereof designed to perform the functions described herein. Furthermore, a controller may be a processor. A processor may be a microprocessor, but in the alternative, the processor may be any conventional processor, controller, microcontroller, or state machine. A processor may also be implemented as a combination of computing devices (e.g., a combination of a DSP and a microprocessor, a plurality of microprocessors, one or more microprocessors in conjunction with a DSP core, or any other such configuration).

The embodiments disclosed herein may be embodied in hardware and in instructions that are stored in hardware, and may reside, for example, in RAM, flash memory, ROM, Electrically Programmable ROM (EPROM), Electrically Erasable Programmable ROM (EEPROM), registers, a hard disk, a removable disk, a CD-ROM, or any other form of computer readable medium known in the art. A storage medium is coupled to the processor such that the processor can read information from, and write information to, the storage medium. In the alternative, the storage medium may be integral to the processor. The processor and the storage medium may reside in an ASIC. The ASIC may reside in a remote station. In the alternative, the processor and the storage medium may reside as discrete components in a remote station, base station, or server.

In certain embodiments, some key features of the BD include:

A.1 The neural net represents a network of interconnected artificial neurons, whose state (activity) evolves in time. The neurons obey dynamical rules, which implies integration of incoming input and activation of the neuron when the input exceeds certain threshold.

A.2 As a result of activation, the neuron sends signals to other neurons in the network by means of synaptic connections (synapses). Synapse represents weighted unidirectional link, which connects two neurons and is oriented from presynaptic to postsynaptic neuron. When active, incoming synapses contribute to the input of the postsynaptic neuron and, therefore, alter its state, e.g. activate the postsynaptic neuron and produce activation of real occupiable space automation device.

Synaptic activity has certain decay times, which allows for implementation of the "switch off" mechanism.

A.3 The neurons are divided into at least three groups: (i) the first group constitutes a core subnetwork of device specific neurons, which directly interacts with and controls occupiable space automation devices. Each artificial neuron in this subnetwork is associated with certain physical device. (ii) The second group of neurons represents a subnetwork of context (state) neurons, which encode the state of environment, e.g. daytime, day of the week, weather condition, etc. The neurons from the second group do not interact with real devices, but they project to device specific neurons from the first group and control their activity. (iii) The 3d group are hidden neurons that may be involved in performing complex associations and generalizations and interconnected with all other neurons.

A.4. The weight (efficiency) of synaptic connections undergo changes during learning stage based on user behavior, or direct input, which constitutes a basis of learning.

Upon reading the following description in light of the accompanying drawing figures, those skilled in the art will understand the concepts of the disclosure and will recognize applications of these concepts not particularly addressed herein. Those skilled in the art will recognize improvements and modifications to the preferred embodiments of the present disclosure. All such improvements and modifications are considered within the scope of the concepts disclosed herein and the claims that follow. The subject matter of the following references are incorporated herein by reference: Bazhenov M, Huerta R, Smith B H (2013) A computational framework for understanding decision making through integration of basic learning rules. The Journal of neuroscience: the official journal of the Society for Neuroscience 33:5686-5697; Hebb D O (1949) The Organization of Behavior New York: Wiley & Sons; Skorheim S, Lonjers P, Bazhenov M (2013) A spiking network model of decision making employing rewarded STDP. PloS one: submitted; Komarov M A, Osipov G V, Burtsev M S (2010) Adaptive functional systems: Learning with chaos. Chaos: An Interdisciplinary Journal of Nonlinear Science, 20:045119.

What is claimed is:

1. A system for occupiable space automation, the system comprising:
    a plurality of periphery devices operatively coupled with at least one controller configured to electronically control operation of at least one occupiable space device; and
    an occupiable space automation control system in electronic communication with the plurality of periphery devices, the occupiable space automation control system comprising a neural network of a plurality of artificial neurons interconnected by a plurality of synapses, the plurality of artificial neurons comprising a device layer associated with and configured to receive input from the plurality of periphery devices and comprising a context layer configured to receive at least one signal indicative of context conditions;
    wherein:
        each artificial neuron of the plurality of artificial neurons comprises a neuron state and a neural input threshold value, and each artificial neuron is configured to receive a first neural input, to alter the neuron state when the first neural input received at the artificial neuron crosses the neural input threshold value, and to initiate at least one response event dependent on the neuron state, the at least one response event providing at least one second neural input to other artificial neurons of the plurality of artificial neurons;
        each synapse of the plurality of synapses interconnects a different pair of artificial neurons, corresponding to the synapse, of the plurality of artificial neurons, and comprises a coupling strength that varies depending on response events of the corresponding pair of artificial neurons within a predetermined time window;
        the occupiable space automation control system is configured to adaptively predict a predicted activity pattern of the plurality of periphery devices based on response events of the plurality of artificial neurons and coupling strengths of the plurality of synapses; and
        the occupiable space automation control system is configured to automatically operate the at least one controller based on the predicted activity pattern.

2. The system of claim 1, being configured to automatically execute an operation upon detection of a deviation from the predicted activity pattern.

3. The system of claim 1, wherein the plurality of periphery devices comprises one or more of the following items (i) to (vi): (i) at least one sensor, (ii) at least one user-activated element, (iii) at least one clock, (iv) at least one timer, (v) at least one camera, and (vi) at least one microphone.

4. The system of claim 1, being configured to automatically operate the at least one controller in response to electronic input received from at least one periphery device of the plurality of periphery devices.

5. The system of claim 1, being configured to receive a user override preventing the occupiable space automation control system from automatically operating the at least one controller based on the predicted activity pattern.

6. The system of claim 1, wherein occupiable space of the occupiable space automation comprises a premises or a vehicle.

7. The system of claim 1, wherein the context conditions comprise environmental conditions, geolocation conditions, or temporal conditions.

8. The system of claim 1, wherein the plurality of artificial neurons comprises a complex connections layer associated with recurrent connections of the context layer and the device layer.

9. A method for occupiable space automation, the method comprising:
    electronically receiving, by at least one first artificial neuron of a device layer of a neural network of an occupiable space automation control system, input from at least one periphery device of a plurality of periphery devices;
    initiating, by the at least one first artificial neuron, a first response event generating a neural input;
    altering a neuron state of at least one second artificial neuron of a context layer of the neural network connected to the at least one first artificial neuron by a synapse if the neural input received by the at least one second artificial neuron crosses a neural input threshold value, wherein the context layer is configured to receive at least one signal indicative of context conditions;
    generating, by the at least one second artificial neuron, a second response event dependent on the neuron state of the at least one second artificial neuron;

altering a neuron state of at least one third artificial neuron of the neural network that is connected by synapses to the at least one first and the at least one second artificial neurons, if a total neural input received by the at least one third artificial neuron from the at least one first and the at least one second artificial neurons crosses the neural input threshold value;

generating, by the at least one third artificial neuron, a third response event dependent on the neuron state of the at least one third artificial neuron;

varying a coupling strength of the synapse dependent on the first, second, and third response events occurring within a predetermined time window;

adaptively predicting, by the occupiable space automation control system, a predicted activity pattern of the plurality of periphery devices based on the first, second, and third response events and the coupling strength of the synapse; and automatically operating, by the occupiable space automation control system, at least one controller of the plurality of periphery devices based on the predicted activity pattern to alter operation of at least one occupiable space device.

10. The method of claim 9, further comprising automatically executing, by the occupiable space automation control system, an operation upon detection of a deviation from the predicted activity pattern.

11. The method of claim 9, wherein the plurality of periphery devices comprises one or more of the following items (i) to (vi): (i) at least one sensor, (ii) at least one user-activated element, (iii) at least one clock, (iv) at least one timer, (v) at least one camera, and (vi) at least one microphone.

12. The method of claim 9, wherein the context conditions comprise environmental conditions, geolocation conditions, or temporal conditions.

13. The method of claim 9, wherein the automatically operating, by the occupiable space automation control system, of the at least one controller of the plurality of periphery devices based on the predicted activity pattern to alter operation of the at least one occupiable space device is responsive to input received from the at least one periphery device of the plurality of periphery devices.

14. The method of claim 9, wherein occupiable space of the occupiable space automation comprises a premises or a vehicle.

15. A non-transitory computer readable medium comprising program instructions for occupiable space automation, wherein the program instructions are configured for:

electronically receiving, at a first artificial neuron of a device layer of a neural network of an occupiable space automation control system, input from at least one periphery device of a plurality of periphery devices;

initiating, by the first artificial neuron, a first response event generating a neural input;

altering a neuron state of a second artificial neuron of a context layer of the neural network connected to the first artificial neuron by a synapse if the neural input received by the second artificial neuron crosses a neural input threshold value, wherein the context layer is configured to receive at least one signal indicative of context conditions;

generating, by the second artificial neuron, a second response event dependent on the neuron state;

varying a coupling strength of the synapse dependent on the first and second response events occurring within a predetermined time window;

adaptively predicting, by the occupiable space automation control system, a predicted activity pattern of the plurality of periphery devices based on the first and second response events and the coupling strength of the synapse; and automatically operating, by the occupiable space automation control system, at least one controller of the plurality of periphery devices based on the predicted activity pattern to alter operation of at least one occupiable space device.

16. The non-transitory computer readable medium of claim 15, wherein the program instructions further comprise automatically executing, by the occupiable space automation control system, an operation upon detection of a deviation from the predicted activity pattern.

17. The non-transitory computer readable medium of claim 15, wherein the plurality of periphery devices comprises one or more of the following items (i) to (vi): (i) at least one sensor, (ii) at least one user-activated element, (iii) at least one clock, (iv) at least one timer, (v) at least one camera, and (vi) at least one microphone.

18. The non-transitory computer readable medium of claim 15, wherein the context conditions comprise environmental conditions, geolocation conditions, or temporal conditions.

19. The non-transitory computer readable medium of claim 15, wherein the automatically operating, by the occupiable space automation control system, of the at least one controller of the plurality of periphery devices based on the predicted activity pattern to alter operation of the at least one occupiable space device is responsive to input received from the at least one periphery device of the plurality of periphery devices.

20. The non-transitory computer readable medium of claim 15, wherein occupiable space of the occupiable space automation comprises a premises or a vehicle.

* * * * *